United States Patent
Hsu (10) Patent No.: US 8,956,446 B2
(45) Date of Patent: Feb. 17, 2015

(54) SEPARABLE SORPTION APPARATUS

(76) Inventor: Tsang-Hung Hsu, Tainan (TW)

(*) Notice: Subject to any disclaimer, the term of this patent is extended or adjusted under 35 U.S.C. 154(b) by 372 days.

(21) Appl. No.: 13/562,586

(22) Filed: Jul. 31, 2012

(65) Prior Publication Data

US 2014/0109608 A1 Apr. 24, 2014

(30) Foreign Application Priority Data

Aug. 5, 2011 (TW) .............................. 100214462 U (51) Int. Cl.
*B01D 53/04* (2006.01)
*B01D 53/18* (2006.01)
*A61L 9/16* (2006.01)

(52) U.S. Cl.
CPC ............ *B01D 53/18* (2013.01); *B01D 53/0415* (2013.01); *B01D 53/0438* (2013.01); *B01D 2253/102* (2013.01); *B01D 2257/80* (2013.01); *B01D 2257/90* (2013.01); *B01D 2258/06* (2013.01); *B01D 2259/40096* (2013.01); *B01D 2259/4508* (2013.01); *A61L 9/16* (2013.01); *A61L 2209/111* (2013.01)
USPC .......................................... 96/117.5; 96/146

(58) Field of Classification Search
CPC .............. B01D 53/04; B01D 53/0415; B01D 53/0438; B01D 53/18; B01D 2253/102; B01D 2257/80; B01D 2257/90; B01D 2258/06; B01D 2259/40096; B01D 2259/4508; A61L 2209/111; A61L 9/00; A61L 9/16
USPC ................. 96/117.5, 143, 146; 422/120, 122
See application file for complete search history.

(56) References Cited

U.S. PATENT DOCUMENTS

| | | | | |
|---|---|---|---|---|
| 2,222,882 A | * | 11/1940 | Shames ........................... | 95/136 |
| 2,765,046 A | * | 10/1956 | Rondholz ....................... | 62/271 |
| 4,127,395 A | * | 11/1978 | McKey et al. .................. | 95/10 |
| 4,211,542 A | * | 7/1980 | Kramer ........................... | 96/128 |
| 5,482,541 A | * | 1/1996 | Maier-Laxhuber et al. . | 96/117.5 |
| 5,673,493 A | * | 10/1997 | Kazakis et al. .................. | 34/80 |
| 6,908,502 B2 | * | 6/2005 | Wireman ...................... | 96/117.5 |

* cited by examiner

*Primary Examiner* — Frank Lawrence
(74) *Attorney, Agent, or Firm* — patenttm.us (57) ABSTRACT

A separable sorption apparatus has a sorption device and a heating device. The sorption device is filled with multiple sorbent granules. The heating device is detachably mounted on the sorption device and has a heater. The sorption device is put in a room that needs dehumidifying or deodorizing. When the sorbent granules have become saturated, the heater of the heating device is mounted into the sorption device to dehumidify or deodorize the sorption device to allow the sorption device to be reused. Since the heating device is detachable, the heating device does not occupy internal space of the sorption device. Thus, the sorption device has ample internal space for receiving the sorbent granules. Consequently, the sorption device has improved sorption effect.

20 Claims, 7 Drawing Sheets

SEPARABLE SORPTION APPARATUS

BACKGROUND OF THE INVENTION

1. Field of the Invention

The present invention relates to a sorption apparatus, especially to a separable sorption apparatus.

2. Description of the Prior Art(s)

In enclosed places, such as bathrooms, closets, storage rooms and the like, of a house, mold and mildew grow easily so causing goods stored in the enclosed places being damped, damaged and rotten. Therefore, to control relative humidity and distinctive odors in the enclosed places is important.

Conventional sorption apparatuses that are used for dehumidifying or removing the distinctive odors have been developed. A conventional sorption apparatus, as disclosed in Taiwan Utility Patent with Patent No. 431585, has a housing and a heating device. The housing is filled with a dehumidifying agent and has multiple ventilation holes formed through an outer wall of the housing. The heating device is assembled in the housing. The conventional sorption apparatus is put in a place where there is a need for dehumidifying, such as a closet. The dehumidifying agent absorbs moisture through the ventilation holes. When the dehumidifying agent is saturated with the moisture, the conventional sorption apparatus is removed from the closet and then the heating device assembled in the housing is switched on to heat the dehumidifying agent and vaporize water from the dehumidifying agent. After the dehumidifying agent is dried, the heating device is switched off and the conventional sorption apparatus is able to be put in the closet again for reusing.

Other conventional regenerative sorption apparatuses, such as disclosed in U.S. Pat. Nos. 6,675,492 and 6,675,421, also have a sorption agent and a heating device, and absorb and adsorb the moisture and the distinctive odors with the sorption agent. After the sorption agent is saturated, the heating device restores the sorption agent to allow the sorption agent to be reused.

To the above-mentioned conventional sorption apparatuses, the sorption apparatus that has more sorption agent has better sorption efficiency. However, the heating device that is securely assembled in the housing of the conventional sorption apparatus and undetachably occupies internal space of the conventional sorption apparatus and the internal space would be more efficiently used if the internal space were to contain more of the sorption agent. When the conventional sorption apparatus is operating, only the sorption agent has the sorption efficiency. The heating device is temporarily not actuated. Therefore, the sorption efficiency of the conventional sorption apparatus is limited and is unable to be improved.

Moreover, since the heating device comprises numerous components such as a heater, a heat sink, multiple insulation sheets, multiple wires and so on, and each conventional sorption apparatus has a heating device, cost of each conventional sorption apparatus is bound to be high. Furthermore, as long as the heating device has the numerous components, the conventional sorption apparatus has complicated assembling processes and breaks down easily.

To overcome the shortcomings, the present invention provides a separable sorption apparatus to mitigate or obviate the aforementioned problems.

SUMMARY OF THE INVENTION

The main objective of the present invention is to provide a separable sorption apparatus. The separable sorption apparatus has a sorption device and a heating device. The sorption device is filled with multiple sorbent granules. The heating device is detachably mounted on the sorption device and has a heater.

The sorption device is put in a room that needs dehumidifying or deodorizing. When the sorbent granules have become saturated, the heater of the heating device is mounted into the sorption device to dehumidify or deodorize the sorption device to allow the sorption device to be reused. Since the heating device is detachable, the heating device does not occupy internal space of the sorption device. Thus, the sorption device has ample internal space for receiving the sorbent granules. Consequently, the sorption device has improved sorption effect.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
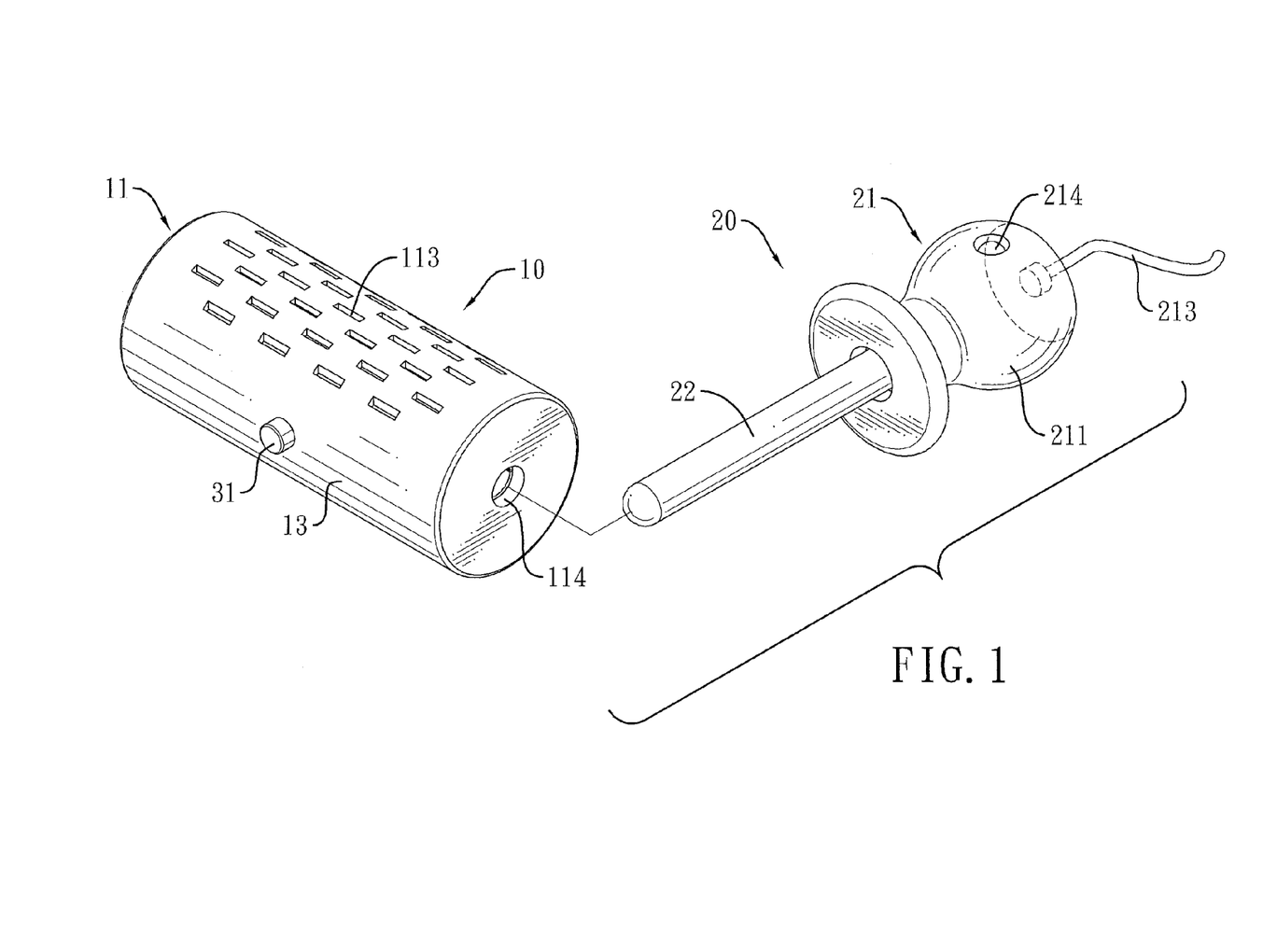
FIG. 1 is an exploded perspective view of a separable sorption apparatus in accordance with the present invention, shown having a first embodiment of a plug.

With reference to FIG. 1, a separable sorption apparatus in accordance with the present invention comprises a sorption device 10 and a heating device 20.

Figure 2:
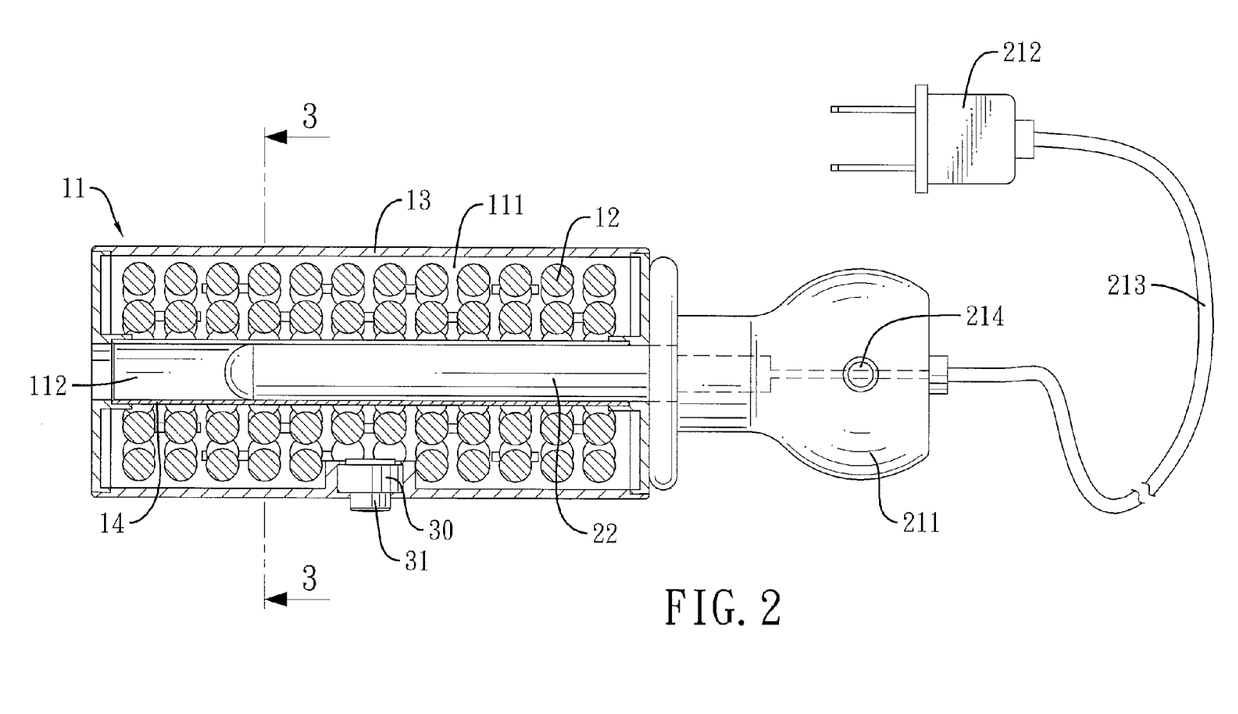
FIG. 2 is a side view in partial section of the separable sorption apparatus in FIG. 1.
Figure 3:
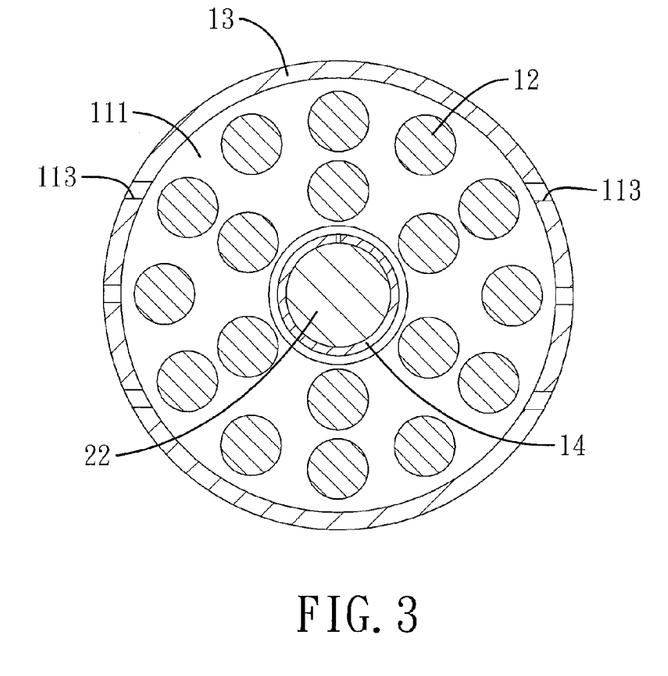
FIG. 3 is a cross-sectional end view of the separable sorption apparatus in FIG. 1, shown having a first embodiment of a conducting tube.

With further reference to FIG. 2, the sorption device 10 has a housing 11, multiple sorbent granules 12 and a sensor 30.

The housing 11 has an outer sidewall, a first chamber 111, a second chamber 112, multiple ventilation holes 113 and at least one opening 114. The first chamber 111 is defined in the housing 11. The second chamber 112 is defined in the housing 11 and is separate from the first chamber 111. The ventilation holes 113 are formed through the outer wall of the housing 11 and communicate with the first chamber 111. The at least one opening 114 is formed through the outer wall of the housing 11 and communicates with the second chamber 112.

With further reference to FIGS. 3, 5, 6, 7 and 8, in the preferred embodiment of the present invention, the housing 11 has an outer casing 13 and a conducting tube 14, 14A, 14B, 14C, 14D. The outer casing 13 forms the outer sidewall of the housing 11. The conducting tube 14, 14A, 14B, 14C, 14D may be circular, rectangular or other shapes in cross-section, is mounted in the outer casing 13 and has an outer surface. The first chamber 111 is defined between the outer casing 13 and the conducting tube 14, 14A, 14B, 14C, 14D. The second chamber 112 is defined in the conducting tube 14, 14A, 14B, 14C, 14D. The ventilation holes 113 are formed through the outer casing 13.

Figure 5:
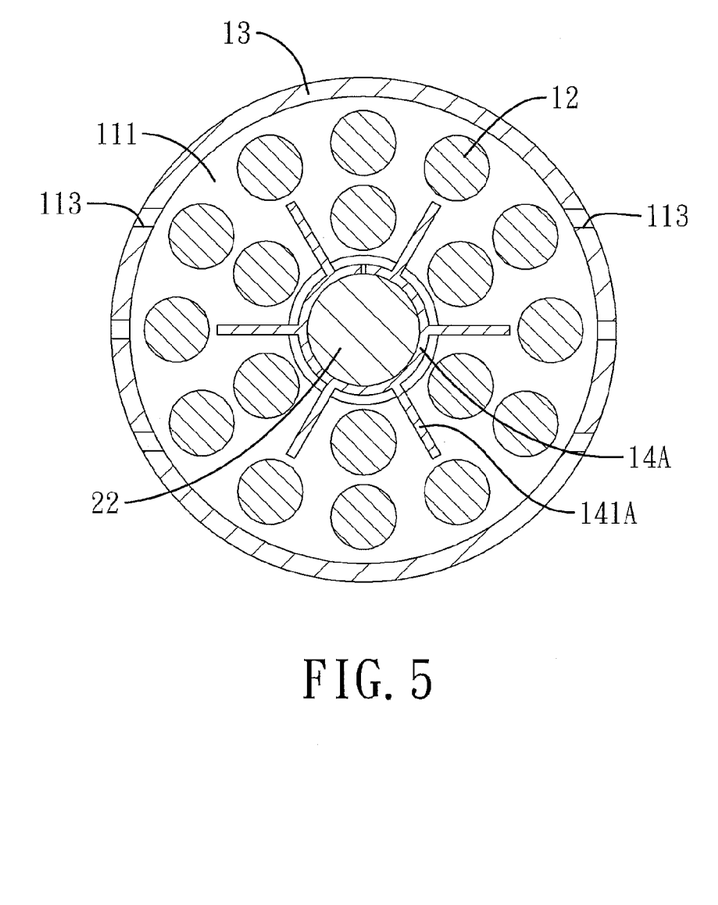
FIG. 5 is a cross-sectional end view of a separable sorption apparatus in accordance with the present invention, shown having a second embodiment of a conducting tube.

With reference to FIG. 5, the conducting tube 14A may further have multiple heat dissipating fins 141A separately protruding from the outer surface of the conducting tube 14A.

Figure 6:
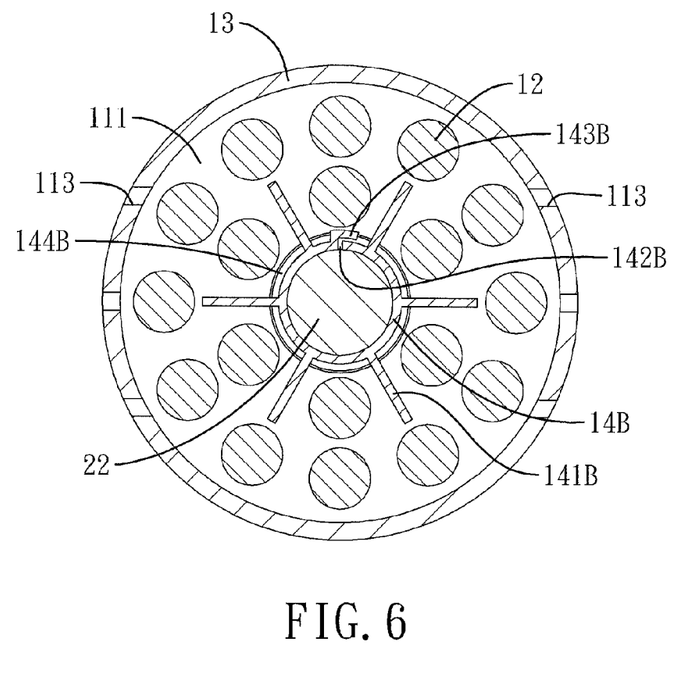
FIG. 6 is a cross-sectional end view of a separable sorption apparatus in accordance with the present invention, shown having a third embodiment of a conducting tube.

With reference to FIG. 6, the conducting tube 14B may further have multiple heat dissipating fins 141B, at least one expansion joint 142B, at least one protrusion 143B and a resilient collar 144B. The heat dissipating fins 141 B separately protrude from the outer surface of the conducting tube 14B. The at least one expansion joint 142B is axially formed through the conducting tube 14B. The at least one protrusion 143B protrudes from the outer surface of the conducting tube 14B, is disposed beside the at least one expansion joint 142B and extends over the at least one expansion joint 142B. The resilient collar 144B is mounted around the conducting tube 14B and is disposed adjacent to an end of the conducting tube 14B.

Figure 7:
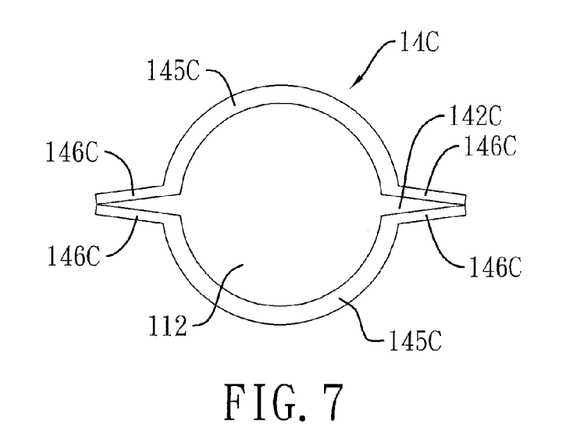
FIG. 7 is an end view of a fourth embodiment of a conducting tube of a separable sorption apparatus in accordance with the present invention.

With reference to FIG. 7, the conducting tube 14C may have two arc panels 145C and two expansion joints 142C. Each of the arc panels 145C is elongated, is arc in cross-section and has two elongated edges and two extending panels 146C. The extending panels 146C respectively protrude from the elongated edges of the arc panel 145C, and respectively and resilient abut the extending panels 146C of the other arc panel 145C. The expansion joints 142C are respectively defined between the elongated edges of the arc panels 145C. The second chamber 112 is defined between the arc panels 145C.

Figure 8:
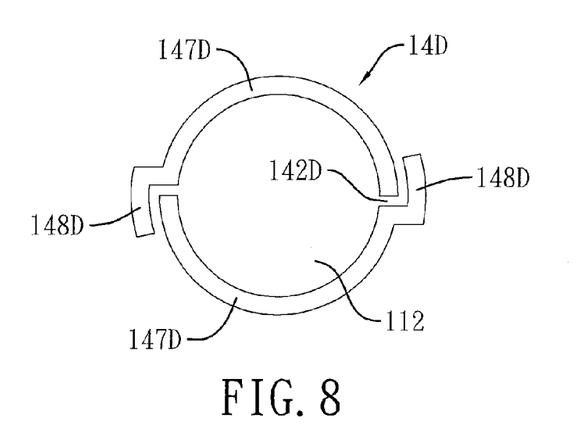
FIG. 8 is an end view of a fifth embodiment of a conducting tube of a separable sorption apparatus in accordance with the present invention.

With reference to FIG. 8, the conducting tube 14D may have two arc panels 147D and two expansion joints 142D. Each of the arc panels 147D is elongated, is arc in cross-section and has a first elongated edge, a second elongated edge and a protrusion 148D. The first elongated edge of the arc panel 147D corresponds to the second elongated edge of the other arc panel 147D. The protrusion 148D protrudes from the first elongated edge of the arc panel 147D and extends over the second elongated edge of the other arc panel 147D. The expansion joints 142D are respectively defined between the first and second elongated edges of the arc panels 147D. The second chamber 112 is defined between the arc panels 147D.

The sorbent granules 12 are deposited in the first chamber 111 of the housing 11, and may be desiccant granules, activated carbon granules or fibers mixed with desiccant and activated carbon.

The sensor 30 is used for determining saturation condition in the sorption device 10, is mounted in the first chamber 111 of the housing 11 and has an indicating portion 31 protruding out of the outer sidewall of the housing 11 and protruding out of the outer casing 13 of the housing 11. Preferably, the sensor 30 may be a chemical sensor and has a chemical, such as cobalt chloride, cobalt bromide, cupric sulfate or the like, that changes colors according to humidity of surroundings. Thus, users determine the saturation condition according to the colors of the chemical visible through the indicating portion 31. Preferably, the sensor 30 may be electrical. The indicating portion 31 may be a display or a light emitting diode (LED). The sensor 30 senses the humidity or concentrations of distinctive odors of the surroundings and shows results on the indicating portion 31.

Figure 4:
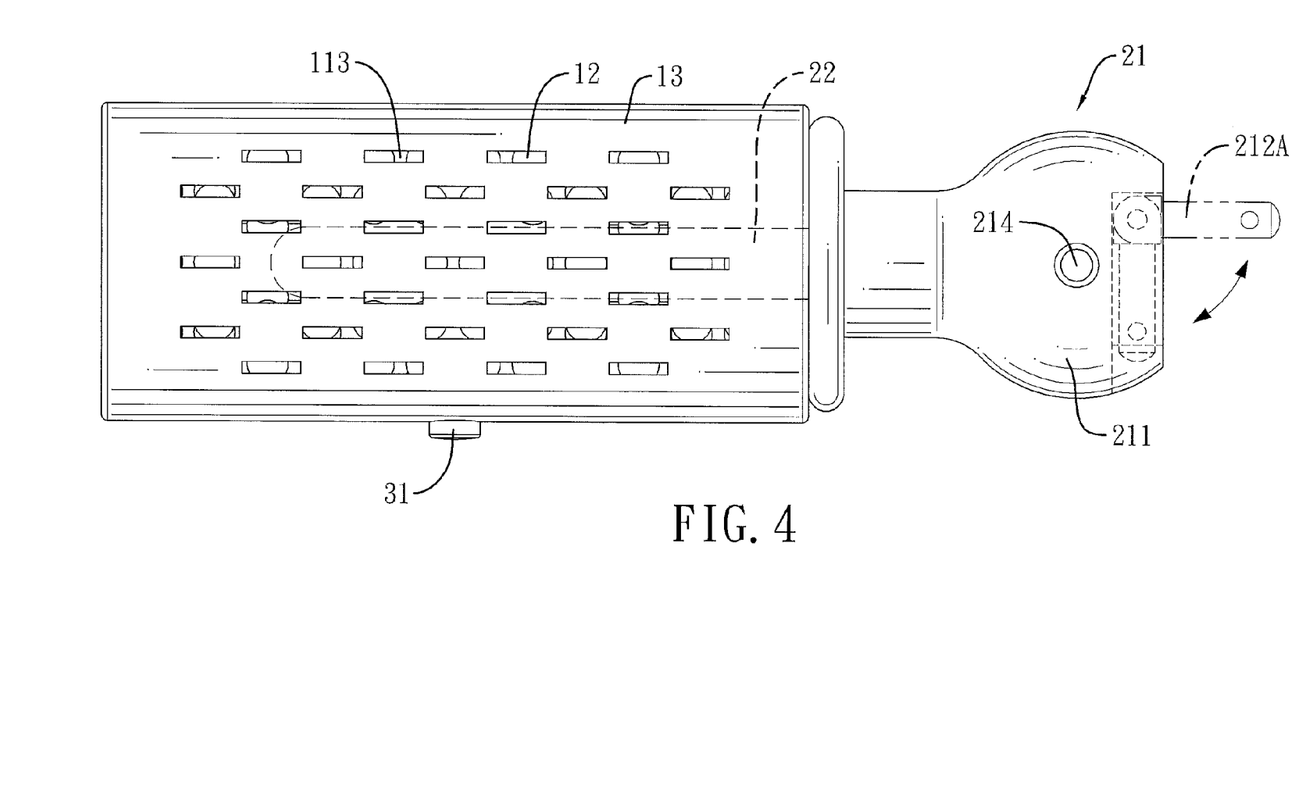
FIG. 4 is an operational side view in partial section of a separable sorption apparatus in accordance with the present invention, shown having a second embodiment of a plug.

With reference to FIGS. 2 and 4, the heating device 20 is detachably mounted on the sorption device 10 and has a base 21 and a heater 22. The base 21 has a main body 211 and a plug 212, 212A. The main body 211 has a power indicating light 214. The plug 212, 212A is electrically connected to the main body 211. The heater 22 is mounted on and is electrically connected to the base 21, is detachably mounted through the opening 114 of the housing 11, and is selectively disposed in the second chamber 112 of the housing 11. With reference to FIG. 2, the plug 212 may be electrically connected to the main body 211 via a wire 213. The heater 22 is electrically connected to the plug 212 via the main body 211 and the wire 213. With reference to FIG. 4, the plug 212A may be pivotally mounted on the main body 211. The heater 22 is electrically connected to the plug 22 via the main body 211.

When using the sorption apparatus, the heating device 20 is detached from the sorption device 10 and the sorption device 10 is put in a room that needs dehumidifying or deodorizing. Take dehumidifying a closet for example. The sorbent granules 12 absorb moisture in the closet through the ventilation holes 113. When the sorbent granules 12 have been saturated with the moisture, the sorption device 10 is taken out of the closet and the heater 22 of the heating device 20 is mounted into the second chamber 112 of the housing 11. Then the heating device 20 is switched on and the power indicating light 214 lights to show the heater 22 is heating the sorbent granules 12 and vaporizing water from the sorbent granules 12. After a period of heating time, the vaporized water is dissipated through the ventilation holes 13. When the sorbent granules 12 are dried, the heating device 20 is detached from the sorption device 10. Then the sorption device 10 is able to be put into and dehumidify the closet again.

The heat dissipating fins 141A, 141B increase contact area of the conducting tube 14A, 14B with the sorbent granules 12 so a vaporizing speed of the sorbent granules 12 is accelerated accordingly.

The resilient collar 144B that is mounted around the conducting tube 14B constricts the conducting tube 14B and narrows a bore of the second chamber 112 via the at least one expansion joint 142B to allow the conducting tube 14B to hold the heater 22 tightly. Thus, heat-conducting efficiency between the heater 22 and the conducting tube 142B is increased.

The sorption apparatus as described has the following advantages. Since the heating device 20 is detachable, the heating device 20 does not occupy internal space of the sorption device 10 when the sorption device 10 is in an absorbing mode. Thus, the sorption device 10 has ample internal space for receiving the sorbent granules 12. Consequently, the sorption device 10 has improved sorption effect. Furthermore, as for a manufacturer, since the sorption device 10 and the heating device 20 are detachable, the manufacturer is able to manufacture the sorption device 10 and the heating device 20 separately. Thus, the sorption apparatus has simplified manufacturing processes and reduced manufacturing cost. Moreover, even if the sorption devices 10 and the heating devices 20 may have defects due to the manufacturing processes, the manufacturer can always choose non-defective sorption devices 10 and heating devices 20 for assembling. Failure rate of the sorption apparatus is consequently reduced. As for the user, the user is able to prepare multiple sorption devices 10 accompanied by one heating device 20. The sorption devices 10 are put in different places and the heating device 20 is capable of restoring all of the sorption devices 10. The sorption apparatus of the present invention is economic and is of benefit to the user.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A sorption apparatus comprising
   a sorption device having
      a housing having
         an outer sidewall;
         a first chamber defined in the housing;
         a second chamber defined in the housing and being separate from the first chamber;
         multiple ventilation holes formed through the outer wall of the housing and communicating with the first chamber; and
         at least one opening formed through the outer wall of the housing and communicating with the second chamber; and
      multiple sorbent granules deposited in the first chamber of the housing; and
   a heating device detachably mounted on the sorption device and having
      a base; and
      a heater mounted on and electrically connected to the base, detachably mounted through the opening of the housing, and selectively disposed in the second chamber of the housing.

2. The sorption apparatus as claimed in claim 1, wherein the sorption device further has a sensor mounted in the first chamber of the housing.

3. The sorption apparatus as claimed in claim 2, wherein the sensor is a chemical sensor.

4. The sorption apparatus as claimed in claim 2, wherein the sensor is electrical.

5. The sorption apparatus as claimed in claim 1, wherein the housing of the sorption device has
   an outer casing forming the outer sidewall of the housing; and
   a conducting tube mounted in the outer casing;
the first chamber of the housing is defined between the outer casing and the conducting tube; and
the second chamber of the housing is defined in the conducting tube.

6. The sorption apparatus as claimed in claim 2, wherein the housing of the sorption device has
   an outer casing forming the outer sidewall of the housing; and
   a conducting tube mounted in the outer casing;
the first chamber of the housing is defined between the outer casing and the conducting tube; and
the second chamber of the housing is defined in the conducting tube.

7. The sorption apparatus as claimed in claim 3, wherein the housing of the sorption device has
   an outer casing forming the outer sidewall of the housing; and
   a conducting tube mounted in the outer casing;
the first chamber of the housing is defined between the outer casing and the conducting tube; and
the second chamber of the housing is defined in the conducting tube.

8. The sorption apparatus as claimed in claim 4, wherein the housing of the sorption device has
   an outer casing forming the outer sidewall of the housing; and
   a conducting tube mounted in the outer casing;
the first chamber of the housing is defined between the outer casing and the conducting tube; and
the second chamber of the housing is defined in the conducting tube.

9. The sorption apparatus as claimed in claim 5, wherein the conducting tube further has multiple heat dissipating fins separately protruding from an outer surface of the conducting tube.

10. The sorption apparatus as claimed in claim 6, wherein the conducting tube further has multiple heat dissipating fins separately protruding from an outer surface of the conducting tube.

11. The sorption apparatus as claimed in claim 7, wherein the conducting tube further has multiple heat dissipating fins separately protruding from an outer surface of the conducting tube.

12. The sorption apparatus as claimed in claim 8, wherein the conducting tube further has multiple heat dissipating fins separately protruding from an outer surface of the conducting tube.

13. The sorption apparatus as claimed in claim 5, wherein the conducting tube further has at least one expansion joint axially formed through the conducting tube.

14. The sorption apparatus as claimed in claim 6, wherein the conducting tube further has at least one expansion joint axially formed through the conducting tube.

15. The sorption apparatus as claimed in claim 7, wherein the conducting tube further has at least one expansion joint axially formed through the conducting tube.

16. The sorption apparatus as claimed in claim 8, wherein the conducting tube further has at least one expansion joint axially formed through the conducting tube.

17. The sorption apparatus as claimed in claim 1, wherein
   the base of the heating device has a main body and a plug electrically connected to the main body; and
   the heater is electrically connected to the plug via the main body.

18. The sorption apparatus as claimed in claim 17, wherein the main body of the base of the heating device has a power indicating light.

19. The sorption apparatus as claimed in claim 17, wherein the plug of the base of the heating device is electrically connected to the main body via a wire.

20. The sorption apparatus as claimed in claim 17, wherein the plug is pivotally mounted on the main body.

* * * * *